United States Patent
Zimmermann

(10) Patent No.: US 7,393,507 B2
(45) Date of Patent: Jul. 1, 2008

(54) APPARATUS FOR TISSUE PROCESSING FOR THE TISSUE EMBEDDING AND MOUNTING FOR THE PROCESSING CONTAINERS FOR TISSUE PROCESSING

(75) Inventor: Michael Zimmermann, Leopoldsdorf (AT)

(73) Assignee: Leica Mikrosysteme GmbH, Vienna (AT)

( * ) Notice: Subject to any disclaimer, the term of this patent is extended or adjusted under 35 U.S.C. 154(b) by 0 days.

(21) Appl. No.: 11/342,437

(22) Filed: Jan. 30, 2006

(65) Prior Publication Data
US 2006/0127280 A1   Jun. 15, 2006

Related U.S. Application Data

(62) Division of application No. 10/100,849, filed on Mar. 18, 2002, now Pat. No. 7,025,934.

(30) Foreign Application Priority Data
Mar. 22, 2001   (EP) .................................. 01107115

(51) Int. Cl.
*B01L 3/00* (2006.01)
(52) U.S. Cl. .............................. 422/102; 422/58; 422/64

(58) Field of Classification Search .................. 422/58, 422/63, 64, 65, 99, 102, 104; 211/41.1; 220/477
See application file for complete search history.

(56) References Cited

U.S. PATENT DOCUMENTS

| 3,165,108 A | | 1/1965 | Elliott et al. | |
| 3,928,140 A | | 12/1975 | Wyatt et al. | |
| 4,347,216 A | * | 8/1982 | Kawasaki et al. | ............. 422/78 |
| 4,688,517 A | | 8/1987 | Hollman | |
| 5,389,339 A | * | 2/1995 | Petschek et al. | ............... 422/64 |

FOREIGN PATENT DOCUMENTS

| DE | 1262887 | 3/1968 |
| GB | 993952 | 6/1965 |

* cited by examiner

*Primary Examiner*—Jill Warden
*Assistant Examiner*—Paul S Hyun
(74) *Attorney, Agent, or Firm*—Simpson & Simpson, PLLC

(57) ABSTRACT

An apparatus (1) for tissue preparation for the tissue embedding, having a transport plate (15) defining a circumferential edge (15c). At the circumferential edge (15c) several recesses (16) are formed, each of which comprises a plurality of several circular cut outs (16a) being arranged so that it has an opening into the direction of the circumferential edge (15c). The transport plate (15) is surrounded by a housing (5) which defines an inner upper side (8a) on which a heating and cooling device (3) is provided.

5 Claims, 4 Drawing Sheets

US 7,393,507 B2

APPARATUS FOR TISSUE PROCESSING FOR THE TISSUE EMBEDDING AND MOUNTING FOR THE PROCESSING CONTAINERS FOR TISSUE PROCESSING

CROSS REFERENCE TO RELATED APPLICATIONS

This application is a divisional application of U.S. patent application Ser. No. 10/100,849 filed Mar. 18, 2002 which issued as U.S. Pat. No. 7,025,934, Apr. 11, 2006. U.S. patent application Ser. No. 10/100,849 claims priority of the European patent application No. 01 107 115.6, filed Mar. 22, 2001, which is incorporated by reference herein.

FIELD OF THE INVENTION

The invention concerns an apparatus for tissue processing for the tissue embedding. Moreover, the invention concerns a mounting for processing containers for tissue processing.

BACKGROUND OF THE INVENTION

The U.S. Pat. No. 4,688,517 discloses an apparatus for processing tissue samples. On a rotatable plate a plurality of processing containers is provided for the sample processing. The plate is rotatable, so that the processing containers can be transported to a processing station at which the tissue samples are successively immersed into different processing liquids. For a suitable tempering of the actually used processing liquids a heating and cooling device is permanently mounted to the housing of the apparatus. The plate is not only rotatable but also raisable and lowerable in the direction of the axle. The processing containers are only snapped into recesses of the transport plate. A firm and defined placement of the processing containers on the plate is not provided.

SUMMARY OF THE INVENTION

It is an object of the invention to provide an apparatus for tissue processing for the tissue embedding which allows a simple and secure handling of the tissue preparation for the tissue embedding.

The above object is solved by an apparatus which comprises:
  a transport plate defining a circumferential edge;
  a plurality of recesses formed in the circumferential edge recesses formed therein, wherein each recess has the form of a circular cut out being so arranged that it has an opening into the direction of the circumferential edge;
  a housing which surrounds the transport plate, wherein the housing defines an inner upper side;
  a heating- and cooling device provided on the inner upper side;
  an indent assigned to each recess; and
  a processing container cooperates with the indent so that a firm and defined placing of each processing container on the transport plate is achieved.

It is a further object of the invention to provide a mounting for the processing containers for tissue processing which comprises:
  a mounting element formed on a bottom of the processing container, wherein the mounting element cooperates with a transport plate defining a circumferential edge;
  a nose formed at the mounting element; and
  an indent at the transport plate, wherein the nose cooperates with the indent when the processing container is in the mounted state.

The above object is solved by a mounting which is characterized in that a nose is formed at the mounting element, wherein the nose stops in the mounted state of the processing container at an indent at the transport plate.

An advantage of the invention is that by the special design of the processing containers and of the transport plate a firm fit of the processing containers is achievable. This firm and defined fit is absolutely necessary for the trouble free tissue processing. The rotation of the transport plate and the raising and lowering of the transport plate make it absolutely necessary, that the processing containers are inserted into the accommodations without cant or touching.

The accommodations are provided with a heating and cooling device which can easily be exchanged, so that the user can switch in a simple manner between processing containers of different size. This is of advantage if large pieces of tissue for the tissue embedding must be processed. In addition, the possibility to pivot the heating and cooling device simplifies the replacement of the entire transport plate substantially easier. The heating and cooling device will thus be lifted away from the free space in the housing. It is not necessary that individual processing containers must be removed from the transport plate in order to enable the replacement. The replacement of the heating and cooling device can be executed particularly easily. For this the pins are to be removed from the hinges and subsequently the entire heating and cooling device is removed. A coding is transmitted to the control unit in the housing, which controls the rotating and the lifting motion of the transport plate accordingly. With the different heating and cooling devices the accommodations for the processing containers are of various sizes and each permanently connected to a power supply for the heating and cooling device. In an embodiment of the invention the accommodation for the processing containers is designed in such a way that a first and a second chamber for the processing containers are provided, whereby the second chamber has a cover. The first chamber serves for tempering the processing liquid in the processing container and for immersing the tissue sample into the processing container. The second chamber can be used for preheating the processing liquid in the processing container. The cover prevents an unnecessary evaporation of the processing liquid.

The indent at the transport plate close to the recesses has the advantage that a defined stop is achievable for the processing containers. The processing containers have a distance element which can be inserted with its narrow side through the openings at the edge of the transport plate. By rotating the processing containers inside of the circular cut out a firm placing is achieved within the recess. The rotating motion is limited in that the nose at the processing container cooperates with the indent on the transport plate.

It is additionally advantageous that the different types of the processing containers have an identical mounting element for attaching the processing containers to the transport plate. The mounting element is symmetrically arranged around the center of a processing container. The mounting element comprises a first and a second circle segment and a first and a second bridge. The first and the second bridge are separated by a distance from each other, which is essentially the size of the opening of the recess at the edge of the transport plate. The diameter of the first and the second circle segment is essentially the same as the diameter of the recess.

BRIEF DESCRIPTION OF THE DRAWINGS

In the drawing the invention is schematically shown and described on the basis of the figures below. The figures show in:

FIG. 3c a cross sectional view of the small processing container taken along line B-B of FIG. 3a;

FIG. 4b a cross sectional view of the large processing container taken along line A-A of FIG. 4a;

FIG. 4c a cross sectional view of the large processing container taken along line B-B of FIG. 4a.

DETAILED DESCRIPTION OF THE INVENTION

Figure 1:
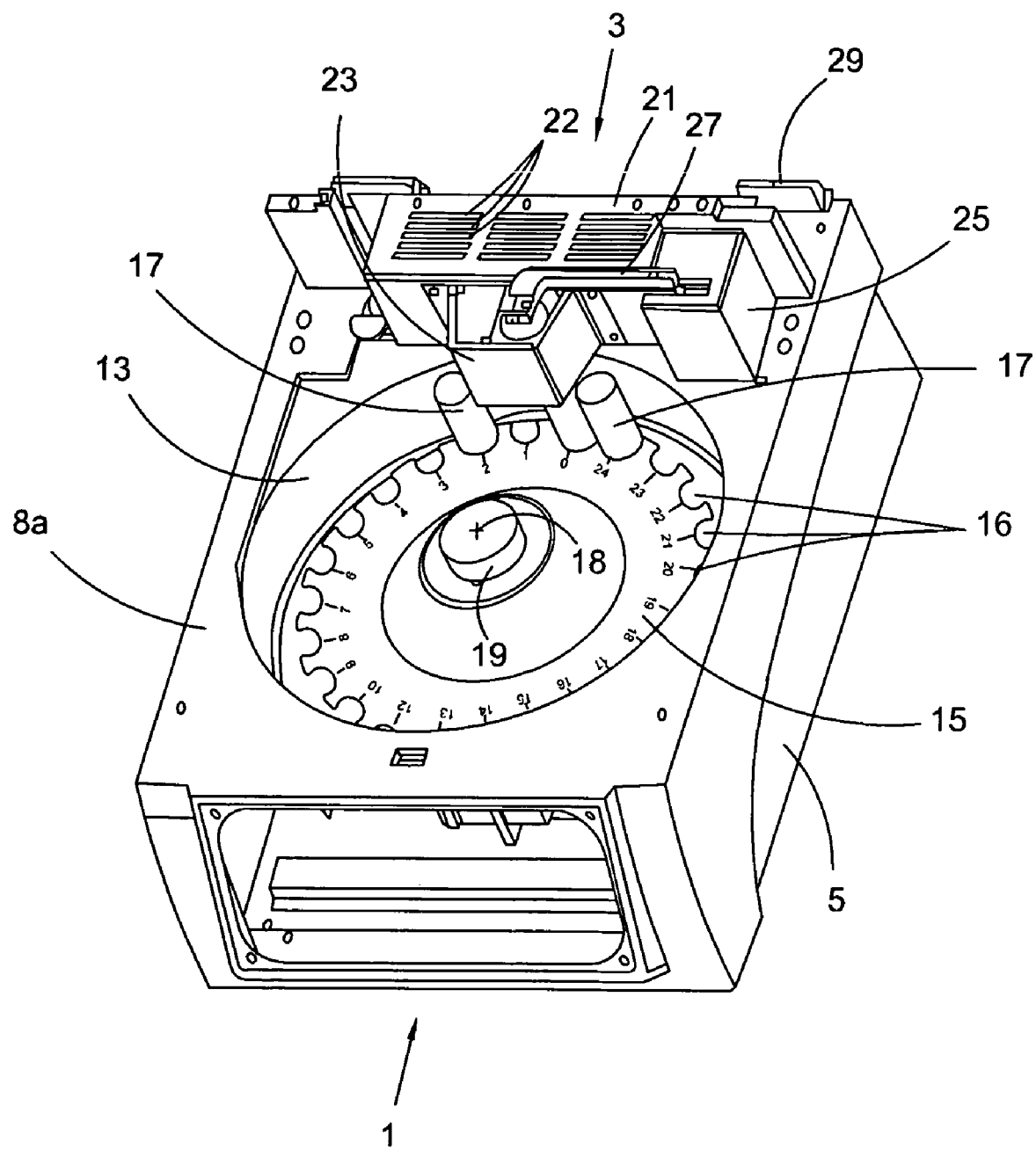
FIG. 1 a perspective view of the apparatus for tissue processing for the tissue embedding.

FIG. 1 shows a perspective view of the apparatus 1 for tissue processing for the tissue embedding without a cover (not shown) provided for the apparatus 1. The housing 5 has formed an inner upper side 8a in which a free space 13 is provided which allows access to the inside of the apparatus 1. By the free space 13 access to the transport plate 15, that is arranged inside the housing 5, is possible. The transport plate 15 is configured in this embodiment in a circular shaped manner and possesses at its edge a plurality of recesses 16, which serve for the accommodation of processing containers 17. On the transport plate 15 processing containers 17 of different size can be mounted. The transport plate 15 is freely rotatable around an axle 18 and can be raised and lowered additionally in the direction of the axle 18. The transport plate 15 is secured by means of a securing element 19. With the housing 5 a heating and cooling device 3 is connected. The heating and cooling device 3 consists of a power supply 21 which is provided with several vent openings 22, for venting off the produced heat. To the power supply 21 an accommodation 23 for the processing containers 17 is attached which is arranged in such a manner that it projects at least partly into the area of the free space 13. As already mentioned above the transport plate 15 can be raised and lowered in the direction of the axle 18. In the raised status at least one processing container 17 is in the accommodation 23 and can be kept in an appropriate way at a specific temperature. The processing containers 17 contain different liquids which are necessary for processing of the tissue samples. Beside the heating and cooling device 3 a mechanic 25 is provided to which an arm 27 is connected. At the arm 27 a tissue sample (not shown) is attached, which is submitted to an appropriate sample processing program. The arm 27 can move up and down whereby the tissue sample is dipped into the liquid, which is in the processing container 17 being in the accommodation 23 at the moment. To the housing 5 hinge elements 29 are connected with which the cover (not shown) can be pivoted. As already mentioned above small processing containers 17a and large processing containers 17b can be used. With respect to the size of the processing container the accommodation 23 is designed.

Figure 2:
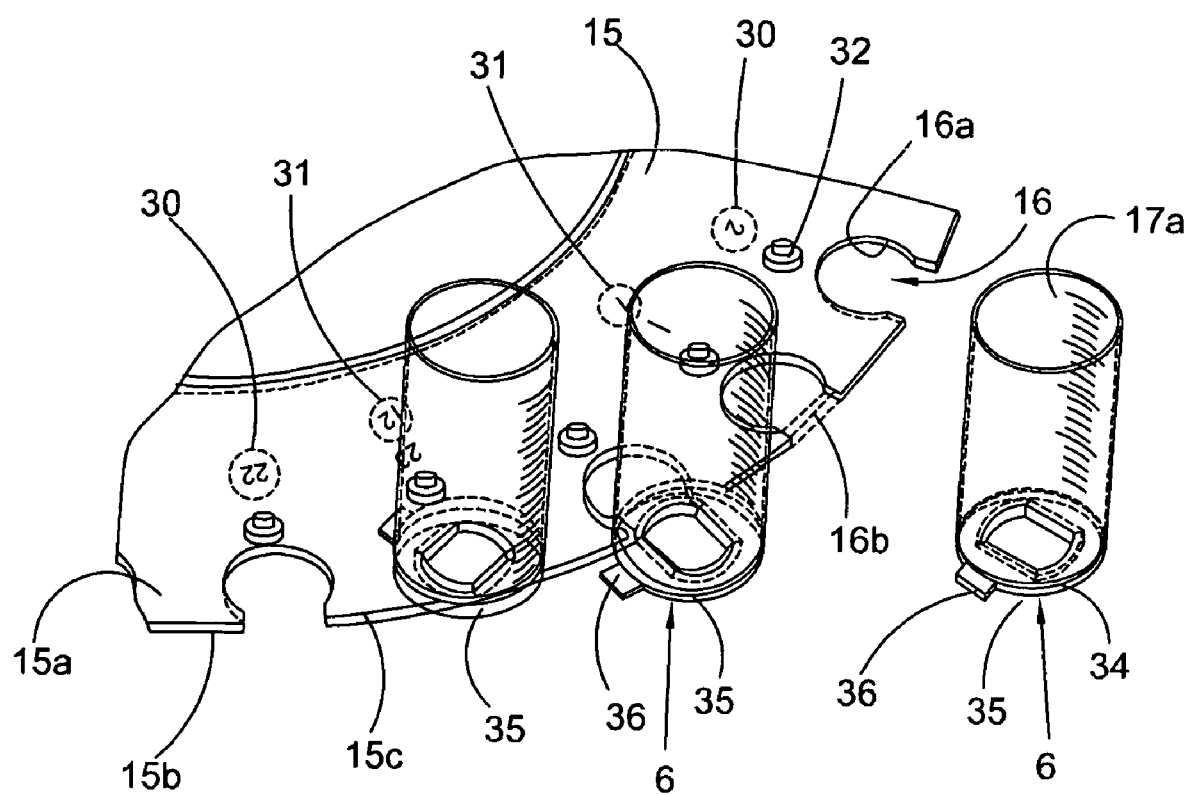
FIG. 2 a perspective partial view of the transport plate together with the processing containers for the tissue embedding.

A partial view of the transport plate 15 is shown in FIG. 2. Hereby the cooperation of the processing container 17 with the transport plate 15 is shown as well. The transport plate 15 comprises an upper side 15a and an under side 15b. On the upper side 15a of the transport plate 15 a first set of numbers 30 is provided directly opposite to the recesses 16. A second set of numbers 31 is provided on the upper side 15a of the transport plate is such that every second recess 16 a number is assigned. The first set of numbers 30 is assigned to the small processing containers 17a (as shown as well in FIG. 2) and the second set of numbers 31 is assigned to the large processing containers 17b. Between the first set of numbers 30 and the recess 16 an indent 32 is formed in the transport plate 15, wherein the indent 32 forms a protrusion on the under side 15b of the transport plate 15. The recess 16 comprises a circular cut out 16a, which has at the circumferential edge 15a of the transport plate 15 an opening 16b, wherein the opening 16b is smaller than the diameter of the recess 16. Preferably, the processing containers 17 are of cylindrical shape and possess at a bottom 33 a circumferential notch 34, which has approximately the thickness of the circumferential edge 15c of the transport plate 15. The notch 34 is terminated at the side opposite to the bottom 33 with a circular disk 35. Within notch 35 is a distance element that is arranged symmetrically around the center of the processing container 17a. The distance element includes opposing first and second circle segments connected with each other by first and second bridges which are parallel to each other. The length of the distance element is essentially the diameter of the recess 16. This can be seen in FIG. 2 in the fully mounted processing container 17 in which the length of the distance element (between each of the peaks of the first and second circle segments) is closely fit within the diameter of recess 16. See also FIGS. 3C and 4C and accompanying description below.) This enables circular disk 35 to rest against under side 15b of transport plate 15. At the circular disk a nose 36 is formed which cooperates with the indent 32 on the under side 15b of the transport plate 15.

Figure 3A:
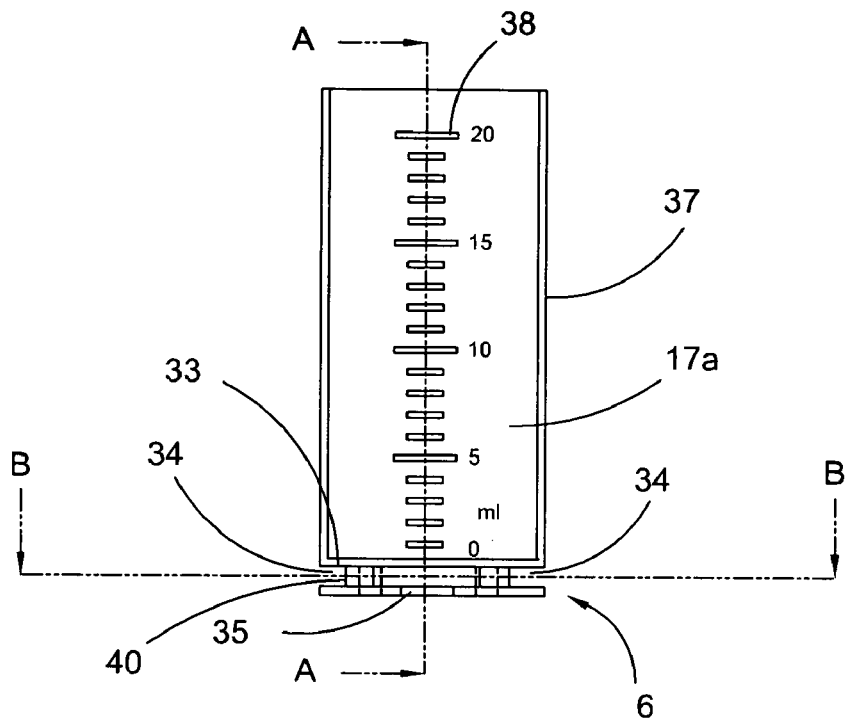
FIG. 3a a side view of a small processing container.
Figure 3B:
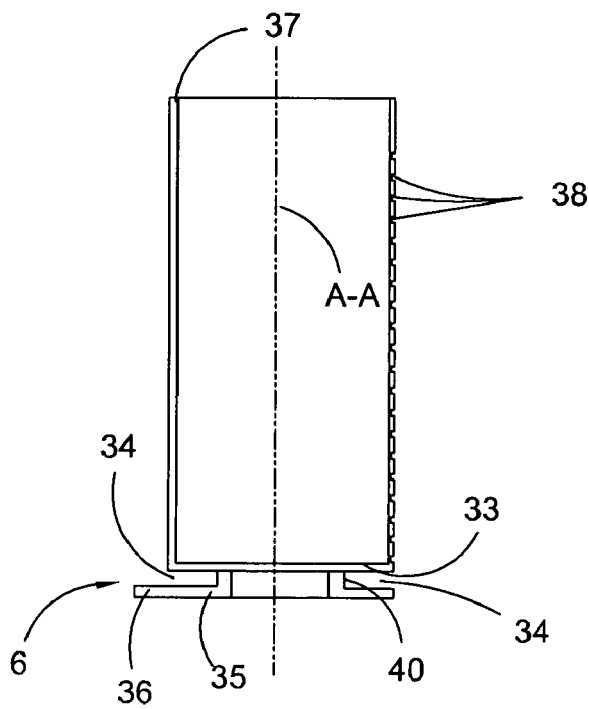
FIG. 3b a cross sectional view of the small processing container taken along line A-A of FIGS. 3a and further showing the processing container mounted on the transport plate.

A side view of the small processing container 17a is shown in FIG. 3a. The small processing container 17a has a cylindrical wall 37 which is covered by a bottom 33. On a part of the cylindrical wall 37 a scale 38 is provided. In this embodiment the scale 38 is pressed into the cylindrical wall 37 of the small processing container 17a. At the bottom 33 a mounting element 6 is formed for holding the processing containers 17 to the transport plate 15. All processing containers 17 have the same mounting element 6. Between the bottom 33 and a circular disk 35 the circumferential notch 34 is formed. In FIG. 3b the small processing container 17a is shown in a cross sectional view along line A-A. The bottom 33 and the disk 35 are separated by the notch 34 so that the distance between the bottom 33 and the notch 34 is approximately the thickness of the edge 15c of the transport plate 15.

Figure 3C:
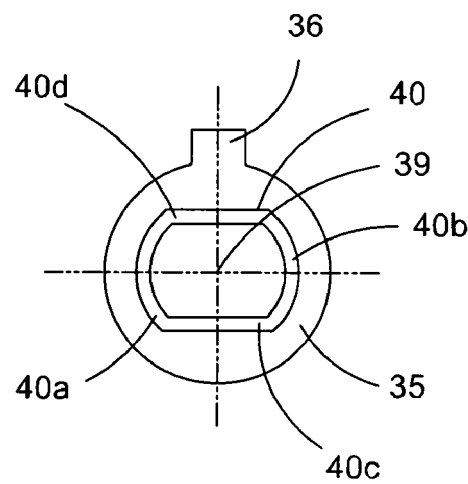

FIG. 3b shows a cross sectional view through the small processing container 17a along line A-A as shown in FIG. 3a. The circular disk 35 possesses at one position a larger diameter. At this position of the circular disk 35 a nose 36 is formed. FIG. 3b also shows circular disk 35 resting against underside 15b of transport plate 15. In FIG. 3c a view of the small processing container 17a along line B-B is shown and clearly shows the shape of a distance element 40 which is formed between the bottom 33 of the processing container 17a and the circular disk 35 by the notch 34. The distance element 40 is arranged symmetrically around the center 39 of the small processing container 17a. In the embodiment shown here, the distance element 40 comprises a first and a second circle segment 40a and 40b which are opposite to each other. The first and the second circle segment 40a and 40b are connected with each other by a first and a second bridge 40c and 40d, wherein the first and the second bridge 40c and 40d are parallel to each other.

Figure 4A:
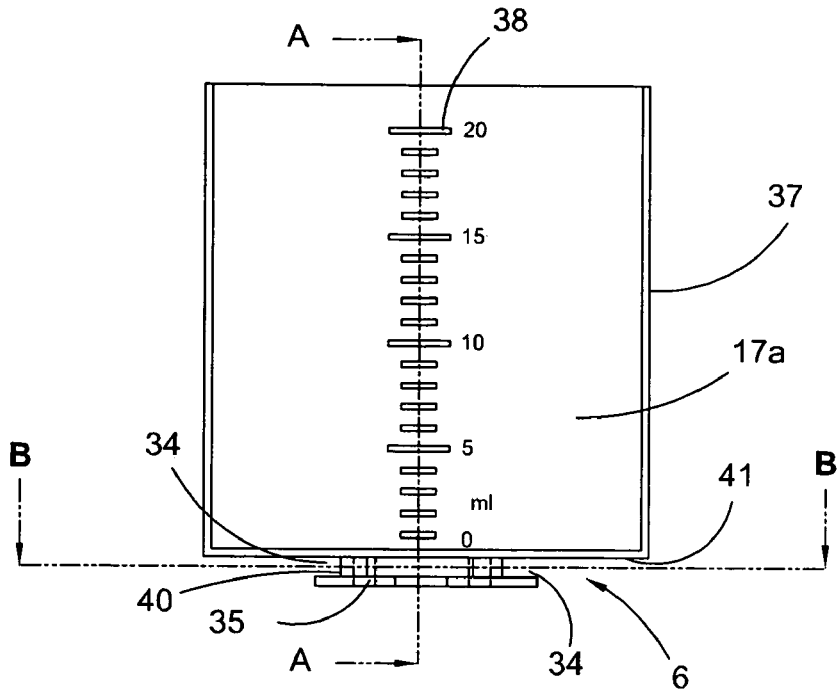
FIG. 4a a side view of a large processing container.
Figure 4B:
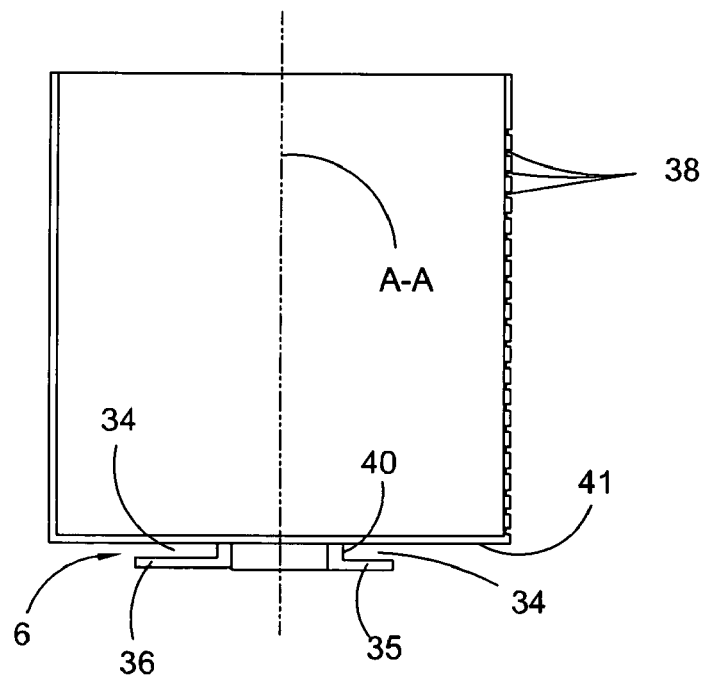
Figure 4C:
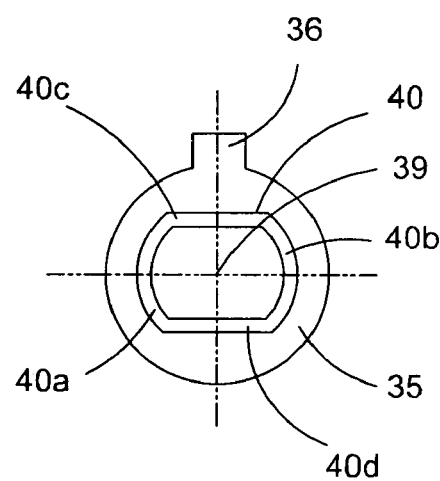

In the FIGS. 4a to 4c the embodiment of a large processing container 17b is shown. All features which are identical with the features as shown in FIGS. 3a to 3d are marked with the same reference numeral. The large processing containers 17b possess the same height as the small processing containers 17a, but differ in diameter. Accordingly, the large processing containers 17b can take up more processing liquid or treat larger tissue samples for processing. As mentioned above the cylindrical wall 37 of the large processing containers 17b is closed with a bottom 41 of a large diameter. As well the circular disk 35 and the circumferential notch 34 are provided adjacent to the bottom 41. The view, as shown in FIG. 4c, clearly indicates that the distance element 40 and the circular disk 35 are dimensioned in the same way as shown in FIG. 3c. This is logical, since the small and the large processing containers 17a and 17b are mounted to the transport plate 15 with the same recess 16.

Moreover, the heating and cooling device 3 (FIG. 1) is exchangeable. This is necessary for the use of different processing containers 17. With the use of large processing containers 17b the accommodation 23, connected to the power supply 21, has to be designed for the reception of the large processing containers 17b as well. To do so, the heating and cooling device 3 can be lifted of in a simple manner and exchanged by another one. Additionally, the heating and cooling device 3 is connected to the inner upper side 8a of the housing 5 by at least one hinge (not shown) in a pivotable manner with the apparatus 1.

The invention was described with respect to a specific embodiment of the invention form. It is however obvious that changes and modifications can be carried out without leaving the scope of protection of the claims below.

PARTS LIST 1 apparatus
3 heating and cooling device
5 housing
6 mounting element
8a inner upper side
13 free space
14 cut out
15 transport plate
15a upper side
15b under side
15c circumferential edge
16 recess
16a circular cut out
16b opening
17 processing container
17a small processing container
17b large processing container
18 axle
19 securing element
21 power supply
22 vent opening
23 accommodation
25 mechanic
27 arm
29 hinge element
30 first set of numbers
31 second set of numbers
32 indent
33 bottom
34 circumferential notch
35 circular disk
36 nose
37 cylindrical wall
38 scale
39 center
40 distance element
40a first circle segment
40b second circle segment
40c first bridge
40d second bridge
41 bottom
A-A line
B-B line

What is claimed is:

1. A mounting for processing containers for tissue processing comprising:
    a transport plate comprising a circumferential edge and an indent;
    a distance element (40) extending between and attached to each of a bottom of said processing container and a mounting element forming a space (notch 34) therebetween, said mounting element comprising a circular disk;
    said distance element comprising a first and a second circle segment and a first and a second bridge connecting the first and second circle segments, said first and second circle segments are opposite each other and have a first diameter, said first and second bridges are parallel and separated by a distance from each other which is essentially of the size of an opening into a circular recess formed at the circumferential edge of said transport plate, said circular recess having a second diameter, said first diameter is essentially the same as said second diameter; and,
    a nose formed on said mounting element;
    wherein the mounting element cooperates with said transport plate defining said circumferential edge; and,
    wherein said nose cooperates with said indent on said transport plate when said processing container is mounted on said transport plate.

2. The mounting as defined in claim 1, wherein the mounting element is symmetrically arranged around a center of the processing container.

3. The mounting as defined in claim 1, wherein the distance between the bottom of said processing container and said mounting element is essentially of the thickness of the circumferential edge of the transport plate, and wherein the nose is formed at the circular disk on the mounting element.

4. The mounting as defined in claim 3, wherein the circular disk rests against the under side of the transport plate.

5. The mounting as defined in claim 4, wherein the indent is provided on the under side of the transport plate.

* * * * *